US011834647B2

(12) United States Patent
Chaung et al.

(10) Patent No.: US 11,834,647 B2
(45) Date of Patent: Dec. 5, 2023

(54) IN VITRO IMMUNE SYNAPSE SYSTEM AND METHOD OF IN VITRO EVALUATING IMMUNE RESPONSE USING THE SAME

(71) Applicant: National Pingtung University of Science and Technology, Neipu (TW)

(72) Inventors: Hso-Chi Chaung, Neipu (TW); Wen-Bin Chung, Neipu (TW); Ann Ying-An Chen, Neipu (TW); Mei-Li Wu, Neipu (TW)

(73) Assignee: National Pingtung University of Science and Technology, Pingtung (TW)

( * ) Notice: Subject to any disclaimer, the term of this patent is extended or adjusted under 35 U.S.C. 154(b) by 421 days.

(21) Appl. No.: 17/021,158

(22) Filed: Sep. 15, 2020

(65) Prior Publication Data

US 2020/0407683 A1 Dec. 31, 2020

Related U.S. Application Data

(62) Division of application No. 16/219,006, filed on Dec. 13, 2018, now abandoned.

(51) Int. Cl.
 *C12N 5/0783* (2010.01)
 *G01N 33/50* (2006.01)
 *C12N 5/0786* (2010.01)
 *G01N 33/68* (2006.01)
 *A01K 67/027* (2006.01)

(52) U.S. Cl.
 CPC ........ *C12N 5/0638* (2013.01); *A01K 67/0278* (2013.01); *C12N 5/0637* (2013.01); *C12N 5/0645* (2013.01); *C12N 5/0646* (2013.01); *G01N 33/5047* (2013.01); *G01N 33/6869* (2013.01); *A01K 2207/15* (2013.01); *A01K 2217/206* (2013.01); *A01K 2227/108* (2013.01); *A01K 2267/0387* (2013.01)

(58) Field of Classification Search
 None
 See application file for complete search history.

(56) References Cited

U.S. PATENT DOCUMENTS

2005/0282148 A1* 12/2005 Warren ................ C12N 5/0698
435/366

FOREIGN PATENT DOCUMENTS

CN 108700582 A 10/2018
TW 201433573 A 9/2014

OTHER PUBLICATIONS

Salem, 2009, Vaccine: 549-557.*
Fischer, 2005, Blood vol. 2828-2835.*
Nadeem Shabir, et al, In Vitro Immune Responses of Porcine Alveolar Macrophages Reflect Host Immune Responses Against Porcine Reproductive Respiratory Syndrome Viruses.
Geng Haidong et al., "Research Progress in Porcine Reproductive and Respiratory Syndrome Virus Immunobiology", Chinese Journal of Wildlife 2012, 33 (4): 236-245, Dec. 31, 2012.
Daniela Wesch et al, "Direct Costimulatory Effect of TLR3 Ligand Poly(I:C) on Human γδ T Lymphocytes", *The Journal of Immunology* 2006;176: p. 1348-1354, Feb. 1, 2006.
Verónica E. García et al, "IL-18 promotes type 1 cytokine production from NK cells and T cells in human intracellular infection", *The Journal of Immunology* 1999; 162: p. 6114-6121, May 15, 1999.
Markey, Kate A. et al., "Imaging the immunological synapse between dendritic cells and T cells", Journal of Immunological Methods. May 9, 2015, 423 (2015) 40-44, elsevier.com.
Davis Daniel M., et al., "What is the importance of the immunological synapse?", Trends in Immunology, Jun. 2004, vol. 25 No. 6, pp. 323-327, sciencedirect.com.
Insights Association, "Control Cell" https://www.insightsassociation.org/issues-policies/glossary/control-cell-0, Oct. 14, 2017.
Laurence Piriou-Guzylack, et al., "Membrane markers of the immune cells in swine: an update" Veterinary Research 39(6):54, 2008, p. 9, Sec. 2.6.
Kenneth C. McCullough, et al., "Phenotype of porcine monocytic cells: modulation of surface molecule expression upon monocyte differentiation into macrophages" Elsevier, Veterinary Immunology and Immunopathology, 58:265-275 (1997).

* cited by examiner

*Primary Examiner* — Amy E Juedes
(74) *Attorney, Agent, or Firm* — Lippes Mathias LLP

(57) ABSTRACT

The present invention relates to an in vitro immune synapse system and a method of in vitro evaluating immune response using the same. The in vitro immune synapse system includes antigen-presenting cells (APCs) and at least one cell type of several specific T cell subtypes isolated from peripheral blood mononuclear cells (PBMCs), all of which is from a same individual of pigs. When a test sample is co-cultured in the in vitro immune synapse system for a given period, it can be determined that the test sample is immunogenic, immunostimulatory or not according to the immunization-related changes of these cells, thereby potentially replacing some kinds of animal experimentation.

6 Claims, 6 Drawing Sheets
Specification includes a Sequence Listing.

SEQUENCE LISTING

<160> NUMBER OF SEQ ID NOS: 6

<210> SEQ ID NO 1
<211> LENGTH: 20
<212> TYPE: DNA
<213> ORGANISM: Artificial sequence
<220> FEATURE:
<223> OTHER INFORMATION: TLR3 forward primer

<400> SEQUENCE: 1
cttgacctcg gccttaatga                                              20

<210> SEQ ID NO 2
<211> LENGTH: 20
<212> TYPE: DNA
<213> ORGANISM: Artificial sequence
<220> FEATURE:
<223> OTHER INFORMATION: TLR3 reverse primer

<400> SEQUENCE: 2
caaggcgaaa gagtcggtag                                              20

<210> SEQ ID NO 3
<211> LENGTH: 20
<212> TYPE: DNA
<213> ORGANISM: Artificial sequence
<220> FEATURE:
<223> OTHER INFORMATION: TLR7 forward primer

<400> SEQUENCE: 3
ttgttccatg tatgggcaga                                              20

<210> SEQ ID NO 4
<211> LENGTH: 20
<212> TYPE: DNA
<213> ORGANISM: Artificial sequence
<220> FEATURE:
<223> OTHER INFORMATION: TLR7 reverse primer

<400> SEQUENCE: 4

```
ggctgaaatt cactgccatt                                          20

<210> SEQ ID NO 5
<211> LENGTH: 20
<212> TYPE: DNA
<213> ORGANISM: Artificial sequence
<220> FEATURE:
<223> OTHER INFORMATION: TLR8 forward primer

<400> SEQUENCE: 5
tctgtcttca aatggcaacg                                          20

<210> SEQ ID NO 6
<211> LENGTH: 20
<212> TYPE: DNA
<213> ORGANISM: Artificial sequence
<220> FEATURE:
<223> OTHER INFORMATION: TLR8 reverse primer

<400> SEQUENCE: 6
gaaagcagcg tcatcatcaa                                          20
```

IN VITRO IMMUNE SYNAPSE SYSTEM AND METHOD OF IN VITRO EVALUATING IMMUNE RESPONSE USING THE SAME

RELATED APPLICATIONS

The present application is a Divisional Application of the U.S. application Ser. No. 16/219,006, filed Dec. 13, 2018, all of which are herein incorporated by reference in their entireties.

A sequence listing is being submitted herein as an ASCII text file with the name "SP-4425-1-US_SEQ_LIST.txt", created on Aug. 31, 2020, with a file size of 1,391 bytes.

BACKGROUND

Field of Invention

The present invention relates to an in vitro simulating immune system and a method of evaluating immune response using the same. More particularly, the present invention relates to an in vitro immune synapse system using various immune cells for in vitro evaluating immune response by various immune cells and a method of in vitro evaluating immune response using the same.

Description of Related Art

The vaccine is a top strategy for controlling all diseases, so it is a main critical issue on global public health to develop safe, effective, and timely available vaccines against pathogens.

Currently, animal experimentations are still necessarily used in testing, screening and finding out antigens and adjuvants with better immune effects during the development of animal vaccines. However, it costs a lot for animal experimentation required for developing vaccines and immune adjuvants. Moreover, the use of animal experimentation in developing vaccines is also limited by the species specificity of animal immune systems, and an experimental result from one species of animals against one pathogen does not necessarily mirror results of other species of animals against other pathogens.

Currently, there are some in vitro cell evaluation platforms in the market, however, these cells on the aforementioned platforms are mostly sourced from mice or commercially available cell lines. As a result, the evaluation results of those platforms cannot replace those from animal experimentation.

To be specific, mice are of small sizes and the number of immune cells taken from each mouse is very limited. The sufficient immune cells required for one test must be collected from different individual mice. However, the co-culture of immune cells from different individuals and species can easily lead to various immune rejections. Therefore, with regard to the immune cells taken from different individuals, evaluation can only be performed by the same type of immune cells, and thus T cell epitope-based evaluation cannot be conducted by the same type of immune cells.

As for commercially available immune cell lines, although there are enough cells, such cell lines are not primary cells, their cellular physiological metabolism, immune responses and the like are distinctly different from those of normal cells. Therefore, the resultant immune responses are quite low in credibility.

Accordingly, it is necessary to develop a system for in vitro evaluating immune response so as to overcome various disadvantages of conventional in vitro cell experimentation, thereby replacing animal experimentation.

SUMMARY

Therefore, one aspect of the present invention provides an in vitro immune synapse system, which includes antigen-presenting cells derived from a same individual pig and at least one cell type of several specific T cell subtypes isolated from peripheral blood mononuclear cells (PBMCs).

Another aspect of the present invention provides a method of in vitro evaluating immune response, which includes co-culturing a test sample in the aforementioned in vitro immune synapse system for a given period, and then detecting the immune synapse system for any immunization-related changes so as to determine whether the test sample is immunogenic, immunostimulatory or not, thereby replacing animal experimentation.

According to the aforesaid aspects of the present invention, an in vitro immune synapse system is provided, which includes antigen-presenting cells and at least one cell type of regulatory T cells, killer cells, and helper T cells. The aforementioned antigen-presenting cells, regulatory T cells, killer cells, and helper T cells are primary cells derived from a same individual, and the number of the antigen-presenting cells can be, for example, larger than the total number of the regulatory T cells, the killer cells and the helper T cells.

According to an embodiment of the present invention, the aforementioned same individual is a specific pathogen free (SPF) pig.

According to an embodiment of the present invention, the aforementioned antigen-presenting cells can be, for example, alveolar macrophages.

According to another aspect of the present invention, a method of in vitro evaluating immune response is provided. In an embodiment, first of all, the aforementioned in vitro immune synapse system is provided, where the in vitro immune synapse system includes, for example, at least one cell type of the antigen-presenting cells, regulatory T cells, killer cells, and helper T cells, as well as control cells, and the antigen-presenting cells, regulatory T cells, killer cells, helper T cells and control cells are primary cells derived from a same individual. Next, the test sample is co-cultured in the aforementioned immune synapse system for 24 to 48 hours. Then, the aforementioned immune synapse system is detected for any immunization-related changes, where the immunization-related changes can be, for example, TLR gene expression level and/or concentration cell cytokine. When an immunization-related change on any one of the regulatory T cells, killer cells and helper T cells has significant difference from an immunization-related change on the control cells, the test sample is determined to be immunogenic or immunostimulatory.

According to an embodiment of the present invention, the aforementioned test sample can be, for example, antigens or adjuvants.

According to an embodiment of the present invention, the aforementioned control cells can be, for example, mononuclear cells.

With application of the in vitro immune synapse system of the present invention and the method of in vitro evaluating immune response using the same, an in vitro immune synapse system including antigen-presenting cells derived from a same individual pig and several specific T-cell subtypes isolated from peripheral blood mononuclear cells is employed to evaluate the T-cell antigen epitope of the test sample. Through the verification of animal experimentation, the aforementioned in vitro immune synapse system does have consistent results with those of animal experimentation. Therefore, when developing new antigens or new adjuvants in the future, the aforementioned in vitro immune synapse system is expected to replace animal experimentation.

It is to be understood that both the foregoing general description and the following detailed description are by examples, and are intended to provide further explanation of the invention as claimed.

BRIEF DESCRIPTION OF THE DRAWINGS

The invention can be more fully understood by reading the following detailed description of the embodiment, with reference made to the accompanying drawings as follows:

FIGS. 2A to 2C depict bar diagrams of mRNA relative expression levels of toll-like receptors (TLRs) 3 (FIG. 2A), TLR7 (FIG. 2B), and TLR8 (FIG. 2C) upon the in vitro co-culturation of the antigen-presenting cell together with the regulatory T cell, the killer cell, the helper T cell and the control cell, respectively, for an individual pig that is immunized by different Porcine Reproductive and Respiratory Syndrome (PRRS) antigens according to an embodiment of the present invention;

FIGS. 3A to 3B depict bar diagrams of the IL-2 (FIG. 3A) level and IL-10 (FIG. 3B) level upon the co-culturation of the antigen-presenting cell with the regulatory T cell, the killer cell, the helper T cell and the control cell, respectively, for an individual pig that is immunized by different PRRS antigens according to an embodiment of the present invention;

FIG. 4 depicts a bar diagram of a TLR mRNA relative expression level of the immune adjuvant that is screened by an in vitro immune synapse system (including porcine helper T cells and alveolar macrophages) according to an embodiment of the present invention.

DETAILED DESCRIPTION

Figure 1A:
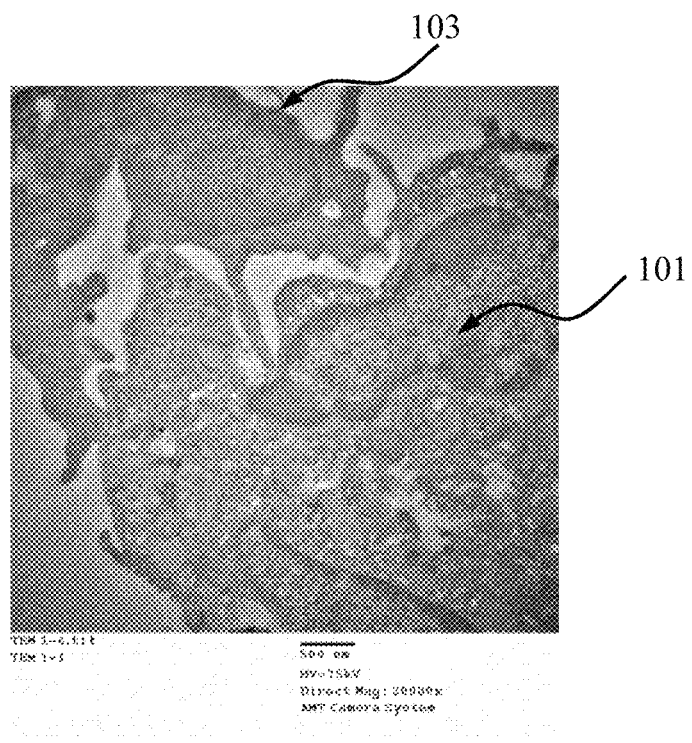
FIGS. 1A to 1D depict transmission electron microscopy (TEM) images (FIGS. 1A to 1C) and scanning election microscopy (SEM) images (FIG. 1D) of a porcine alveolar macrophage matching to a regulatory T cell (FIGS. 1A and 1B) or matching to a helper T cell (FIGS. 1C and 1D) according to an embodiment of the present invention.

Reference will now be made in detail to the present embodiments of the invention, examples of which are illustrated in the accompanying drawings. Wherever possible, the same reference numbers are used in the drawings and the description to refer to the same or like parts.

As aforementioned, the present invention provides an immunological synapse (IS) system and the method of in vitro evaluating immune response using the same, the system being an immunological synapse system including antigen-presenting cells (APCs) derived from a same individual pig and several specific T-cell subtypes isolated from peripheral blood mononuclear cells (PBMCs), which is used to evaluate the T-cell epitope of a test sample.

To be specific, the immunological synapse (IS) mentioned here in the present invention refers to the one formed by APCs and the T-cell subtypes of PBMCs in vitro. The aforementioned immunological synapse (IS), which is a hypothesis proposed by researchers in recent years, is defined as a stable and collaborative interaction between two or more types of cells in the immune system, and causes consequent responses of at least one cell type of the cells. This IS system fully covers essential factors required for the in vivo immune responses of an animal, including integration information between APCs and different T-cell subtypes (such as an antigen identification system), soluble factors with guiding functions (such as cell cytokines), and the intermolecular interaction for forming specific immune responses (such as the intercellular receptor-ligand binding system).

APC plays a critical role in initiating and maintaining the immune response. APC identifies a pathogen recognition molecular pattern (PAMP) by the pathogen recognition receptor (PRR) of an immune system, and initiates a specific immune path through signaling transduction. When APC is activated by antigens or adjuvants, profiles of various cytokines or proinflammatory cytokines are generated through identification of PRR, so as to influence the differentiation and proliferation of various T-cell subtypes, all of which can determine that the immune response trends to what kind of the immune cell or what pattern of proinflammatory cell response.

The toll-like receptor (TLR) is the major family of PRRs. In recent years, researches on APC and TLR have provided a great deal of new information about the development of immune mechanisms and vaccines/adjuvants both related to a TLR agonist. The TLR agonists and the cell cytokines can change the micro-environment in which the APCs contact the T cells, thereby affecting the stability during the IS formation between the two cells. The deeper we discover the effect of the TLR agonists and cell cytokines on the IS formation between a specific antigen or infected APCs and the T cells, the more we can effectively apply the TLR agonists and cell cytokines on the immune adjuvant of animal vaccines.

There are kinds of TLR agonists now being attempted as the immune regulator or an active ingredient in the immune adjuvant, but a specific cell cytokine is required to involve in the micro-environment in which the APC contacts the T cells, so as to form a stable IS. However, the research on how the interaction between TLR agonist and cell cytokine affects the IS formation is rare.

In an embodiment, an in vitro immune synapse system of the present invention can include antigen-presenting cells and several specific T-cell subtypes isolated from PBMCs, the embodiment of which can include but be not limited to at least one cell type of regulatory T (Treg) cells, natural killer (NK) cells, and T helper (Th) cells. In other embodiments, the in vitro immune synapse system can also include an antigen-presenting cells; at least one cell type of a regulatory T cell, a killer cell and a helper T cell; and a control cell.

One of characteristics of the present invention is that the antigen-presenting cell, the regulatory T cell, the killer cell, the helper T cell and the control cell are primary cells derived from a same individual, thereby overcoming the immune rejection. In an embodiment, the aforementioned same individual can be, for example, a specific pathogen free (SPF) pig of any known breeds. Primary cells taken from the SPF pig can exclude interference of other antigens or antibodies. If the cells were not taken from the SPF pig, the test result of the antigen-presenting cells and the several specific T-cell subtypes isolated from peripheral blood mononuclear cells might be disturbed or even not able to obtain a result consistent with the animal experimentation.

The antigen-presenting cells referred in the present invention are not limited to their origin from body parts, depending on test samples. In some specific examples, the antigen-presenting cells can be alveolar macrophages (or referred to as alveolar cells); Langerhan's cells of skin; interdigitating cells (IDCs) of thymus; dendritic cells (DCs), activated B cells, macrophages and the like in the spleen and lymph nodes.

Preferably, the regulatory T cells referred in the present invention have preferably at least $CD4^+/CD25^+$ cell marker. The killer cells have preferably at least $CD4^-/CD25^+$ cell marker. The helper T cells have preferably at least $CD4^+/CD25^-$ cell marker. There is no limitation on cell types of the control cells; however, the control cells have preferably at least $CD4^-/CD25^-$ cell marker, and in an example, they can be mononuclear cells.

In the aforementioned in vitro immune synapse system, the number of antigen-presenting cells is preferably larger than the total number of regulatory T cells, killer cells and helper T cells. Preferably, the number of antigen-presenting cells can be 2 to 10 times of total number of regulatory T cells, killer cells and helper T cells. In other embodiments, the number of antigen-presenting cells can also be larger than total number of regulatory T cells, killer cells, helper T cells and control cells. Preferably, the number of antigen-presenting cells can be 2 to 10 times of the total number of regulatory T cells, killer cells, helper T cells and control cells.

The aforementioned in vitro immune synapse system can be applied to the method of in vitro evaluating immune response. In an embodiment, first of all, the aforementioned in vitro immune synapse system is provided.

Next, the test sample is co-cultured in the aforementioned immune synapse system for a given period. The test sample referred to in the present invention can be, for example, antigens or adjuvant, wherein types of the antigens and adjuvant should be known to one of ordinary skills in the art of the present invention rather than being recited herein.

The co-culturation referred in the present invention can include matching the antigen-presenting cells to any of several specific T-cell subtypes isolated from PBMCs, for example, matching the antigen-presenting cells to the regulatory T cells, the antigen-presenting cells with the helper T cells, and the antigen-presenting cells with the killer cells.

In the aforementioned embodiment, the aforementioned co-culturation can be implemented in a cell culture medium suitable for antigen-presenting cells and peripheral blood mononuclear cells. In general, the kinds of the cell culture medium is not limited but can be commercial products such as RPMI 1640 medium with 10% of pig serum or not.

In the aforementioned embodiment, a given period of the aforementioned co-culturation can be, for example, 6 to 24 hours, or 12 to 24 hours, or preferably 18 to 24 hours, and more preferably 24 hours.

Then, the immunization-related changes are to be evaluated after co-culturation of the aforementioned matched cells.

Then, the aforementioned immune synapse system is detected for any immunization-related changes. In general, the detection items for immunization-related changes are not limited, which can be, for example, a toll-like receptor (TLR) gene expression level, cytokine concentration and so on in an embodiment. The TLR gene expression level recited in the present invention can include but not limited to the TLR3 gene expression level, TLR7 gene expression level and/or TLR8 gene expression level. The cell cytokine concentration referred in the present invention can be, for example, the interleukin (IL) concentration, including but being not limited to IL-2 concentration and/or IL-10 concentration.

When the immunization-related changes of any one of regulatory T cells, killer cells, helper T cells significantly differ from the immunization-related changes of control cells, it can be determined the aforementioned test sample is immunogenic or immunostimulatory. The significant difference described in the present invention refers to the statistically significant difference, typically $P<0.05$.

Taking the porcine reproductive and respiratory syndrome virus (PRRSV) as an example, the PRRSV is a major cause leading to serious respiratory symptoms of pigs in Taiwan. Once affected by PRRSV, a pig will be subjected to a high death rate, thereby extremely lowering the pig farm productivity. PRRSV mainly affects pig APCs, especially immune functions between APCs affected by viruses and regulatory T cell (Treg) cells, changes immune cell activity, induces the differentiation and hyperplasia of different T-cell subtypes, reduces the antivirus immune response of the host, and thus makes the PRRSV avoid the host immune function. In recent years, the high pathogenic (HP) PRRSV has further caused serious porcine respiratory symptoms and great economic losses to the pig farming industry. Therefore, in the respiratory mucosa immune system, it is the most important topic regarding to enhancing the mucosa immune vaccine development that the antigen-presenting cell (APC) immune activity of the respiratory mucosa immune system is activated. The respiratory mucosa immune system has alveolar macrophages as a primary first defense line of cells which are related to the interaction between a TLR agonist/cell cytokine and different T-cell antigen epitopes, but mechanisms used for their application in the animal mucosa immune IS formation and regulation are still outstanding. However, according to the verification of animal experimentation, the in vitro immune synapse system of the present invention does have results consistent with those of animal experimentation. Therefore, when developing new antigens or new adjuvant in future, the aforementioned in vitro immune synapse system is expected to replace animal experimentation.

The applications of the present invention are illustrated by several following embodiments, but do not intend to limit the present invention thereto. Various changes and modifications can be made by one of ordinary skills in the art of the present invention, without departing from the spirit and scope of the present invention.

Example 1. Establishing In Vitro Immune Synapse System 1.1 Isolation of Peripheral Blood Mononuclear Cells (PBMCs)

In this Example, the porcine PBMCs were isolated from a 4-week-old SPF pig (of a breed multiplied between Landrace and Yorkshire) by known methods. It should be mentioned that the age and strains of the aforementioned SPF pig were merely illustrative while not limited to the aforementioned, and pigs of other ages and breeds could also be used.

Firstly, blood was collected from the jugular vein of the neck of the SPF pig, by a 20 mL blood collection syringe containing 1 mL of 0.5M EDTA. Then, the blood was aliquoted and centrifuged for 25 minutes, from which a buffy coat was taken and uniformly mixed with Hank's balanced salt solution (HBSS, free of calcium and magnesium ions) at a ratio of 1:2. Next, the cell mixture solution was slowly poured onto a Ficoll-Hypaque™ lymph cell separation medium and centrifuged under 4° C. at 900×g for 30 minutes. After that, the PBMC layer was collected, then rinsed for 3 times by HBSS, adjusted its cell concentration by a RPMI-1640 cell culture medium containing 10% of pig serum (abbreviation as PS-RPMI), and then placed and cultured in an incubator under 37° C. for later use.

1.2 Sorting and Culturing of Pig T-Cell Subtypes

The aforementioned and isolated porcine PBMCs were collected the cell density of the cell solution were adjusted well, followed by adding the anti-porcine CD4 antibody and anti-porcine CD25 antibody into the cell solution, reacting the cell solution with the secondary antibodies, the cell solution was centrifuged at a 1000×g for 5 minutes. Removing the supernatant, phosphate buffered solution (PBS) was added to resuspend the cell pellet, and Coulter Epics Altra Flow Cytometry (Beckman Coulter, CA, USA) was used to analyze cell surface marks and sort cells. After the collection of the target cells, they were centrifuged to remove the supernatant, rinsed cells for 3 times by PBS, and added with PS-RPMI culture solution so as to resuspend the cells, and then placed and cultured them in an cell incubator under 37° C. In addition, the cell solution was added with the anti-porcine CD4 and anti-porcine CD25 antibodies, and sorting quadrants were set by computer, in order to obtain the cell markers CD4$^+$/CD25$^-$ (i.e., Th cell), CD4$^-$/CD25$^+$ (i.e., NK cell), CD4$^+$/CD25$^+$ (i.e., Treg cell), and CD4$^-$/CD25$^-$ (i.e., control cell). The aforementioned cells were centrifuged to remove the supernatant, and then rinsed for 3 times by PBS, and added into the PS-RPMI medium to resuspend the cells, placed them into a cell incubator under 37° C. for culturation.

1.3 Isolation of Porcine Alveolar Macrophages

In this Example, a SPF pig was anesthetized and immediately its lungs were excised. 200 mL of PBS was injected into the lungs through an endotracheal tube for rinsing and gently rubbing the lungs, and then the flushing fluid was collected. The flushing fluid was collected by a 50 mL plastic centrifuge tube, and centrifuged under 4° C. at 200×g for 10 minutes, thereby collecting the cells deposited at the bottom, resuspend the cells in the PS-RPMI cell culture medium, and adjusting the cell concentration for subsequent use as antigen-presenting cells.

1.4 Evaluation of In Vitro Immune Synapse System

In this Example, alveolar macrophages were respectively cultured in a 24-well cell culture plate with the RPMI-1640 culture medium, in which each well had 0.5 mL of antigen-presenting cell suspension (1×10$^7$ cells/mL). After cultured in an incubator containing 5% $CO_2$ under 37° C. for 24 hours, the cells were added with different sorted T-cell subtypes (i.e. Treg cells, Th cells, NK cells and control cells), respectively. Each T-cell subtype was adjusted to 1×10$^6$ cells/mL, and 0.5 mL/well of cells for co-culture was added with antigen protein (2 µg/10 µL/well), and then added with the RPMI-1640 culture medium to a total volume of 1 mL for co-culture for 24 hours. During this evaluation, two repeats were used to identify the influence of different culture durations and antigen concentrations on the IS formation. The cells were then reacted with 4-fold volume of 2% paraformaldehyde under 4 pa for 20 minutes of incubation, then added with equal volume of ammonium chloride under the room temperature for 20 minutes of incubation, followed by centrifuged at 500×g for 10 minutes. The cell layer was collected, added with fixed buffer solution, placed on ice for 10 minutes of incubation, and then analyzed for IS formation by the election microscopy.

The immunological synapse was a stable junction formed by antigen-presenting cells and target T cells, and also played a key role in the activation of the immune system. The interaction between macrophages and T cells and the synapse structure formed by the two cells could be observed by transmission electron microscopy (TEM) and scanning election microscopy (SEM).

Referring to FIGS. 1A to 1D, which were depicted TEM images (FIGS. 1A to 1C) and SEM image (FIG. 1D) of a porcine alveolar macrophage 101 matching to a regulatory T cell 103 (FIGS. 1A and 1B) or matching to a helper T cell 105 (FIGS. 1C and 1D) according to an embodiment of the present invention.

Figure 1B:
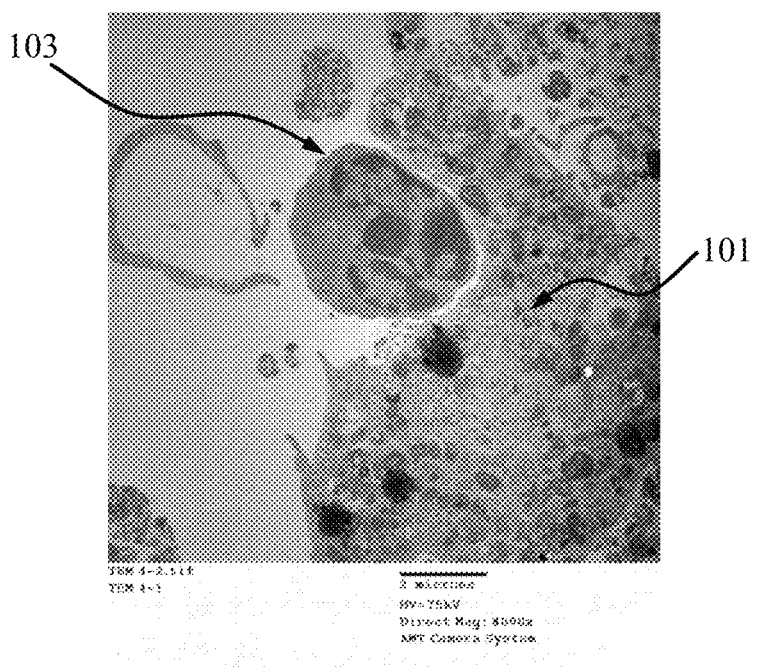
Figure 1C:
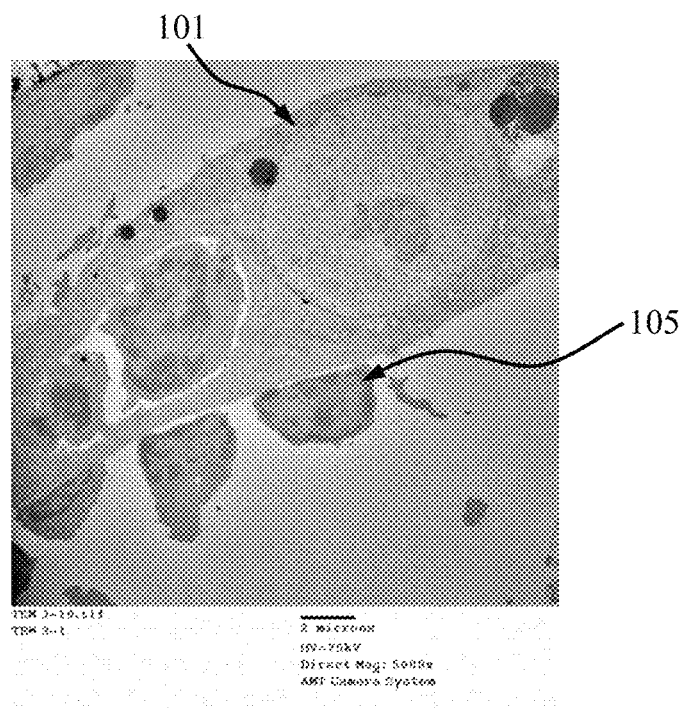
Figure 1D:
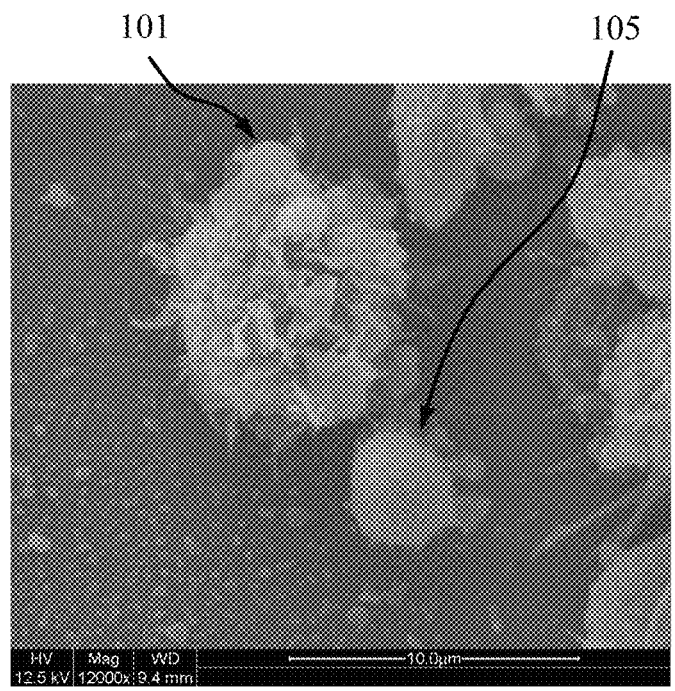

As shown in the results of FIGS. 1A to 1D, during the first stage of the co-culture, the regulatory T cell 103 would extend pseudopodia toward the alveolar macrophage 101 (as shown in FIG. 1A). During the second stage, the alveolar macrophage 101 and the regulatory T cell 103 showed centriole proximity (as shown in FIG. 1B). During the third stage, the Golgi complex of the alveolar macrophage 101 enlarged, the interface between the two cells was flatten (as shown in FIG. 1C) and formed to the immunological synapse (as shown in FIG. 1D), proving that the two cells were able to form the immune synapse system in vitro.

Example 2. Verification of Immune Synapse System by Animal Experimentation

Twelve 4-week-old SPF pigs were divided into 3 groups (4 per group), including respectively a negative control group, a "antigen 1" group without T-cell epitope (free of T-cell antigen epitope; PRRSV-1), and an "antigen 2" group (containing T-cell antigen epitope; PRRSV-2), respectively, all groups being subjected to pig immunization plan which included the first immunization on the pigs of 4 weeks old and the second immunization on the pigs of 6 weeks old. The "antigen 1" did not contain specific T-cell antigen epitope additionally, and the "antigen 2" contained specially T-cell antigen epitope additionally that was designed by inventors, wherein the T-cell antigen epitope of PRRSV as "antigen 2" had a sequence designed by the inventors. However, PRRSV-1 and PRRSV-2 were merely illustrative examples for verifying the immune synapse system, and other known sequences could also be used without repeatedly described herein.

The aforementioned SPF pigs were sacrificed at 8 weeks old, and the alveolar macrophages and PBMCs were isolated respectively, in which the alveolar macrophages were used as the antigen-presenting cell (APC) which was then co-cultured with specific T-cell subtypes (i.e., Th cell, NK cell, Treg cell and control cell) sorted from the blood PBMCs by a flow cytometry, for providing evaluation on its function influenced by the animal immunization. The TLR gene expression and cell cytokine of the in vitro immunological synapse were analyzed for verification of the in vitro immunological synapse as screening platforms in later use.

2.1 Evaluation of Changes in TLR Gene Expression

The TLR gene expression level of the aforementioned specific T-cell subtypes upon immunostimulation was measured by the following or conventional methods. Firstly, total RNA of the aforementioned specific T-cell subtypes was extracted by Trizol® reagent and Direct-Zol® column. After quantification by a spectrophotometer, a commercial kit [such as PrimeScript™ RT reagent kit (Takara)] was used for synthesizing cDNA according to operation steps of the kit. Briefly, 0.5 μg of RNA was added into 2 μL of 5×PCR buffer solution, 0.5 μL of PrimeScript™ RT enzyme mix I, 0.5 µL of oligo-dT primer (50 µM), 0.5 µL of random primer (100 µM). The volume of each reaction was added to 10 µL by double distilled (dd) $H_2O$, and it was then treated under 42° C. for 30 minutes. The expression level of TLR gene could be determined by the following primers and real time PCR.

The upstream primer of TLR3 gene was a sequence listed as SEQ ID NO: 1, while the downstream primer of TLR3 gene was a sequence listed as SEQ ID NO: 2. The upstream primer of TLR7 gene was a sequence listed as SEQ ID NO: 3, while TLR7 gene downstream primer was a sequence listed as SEQ ID NO: 4. The upstream primer of TLR8 gene was a sequence listed as SEQ ID NO: 5, while the downstream primer of TLR8 gene was a sequence listed as SEQ ID NO: 6.

Figures 2A, 2B:
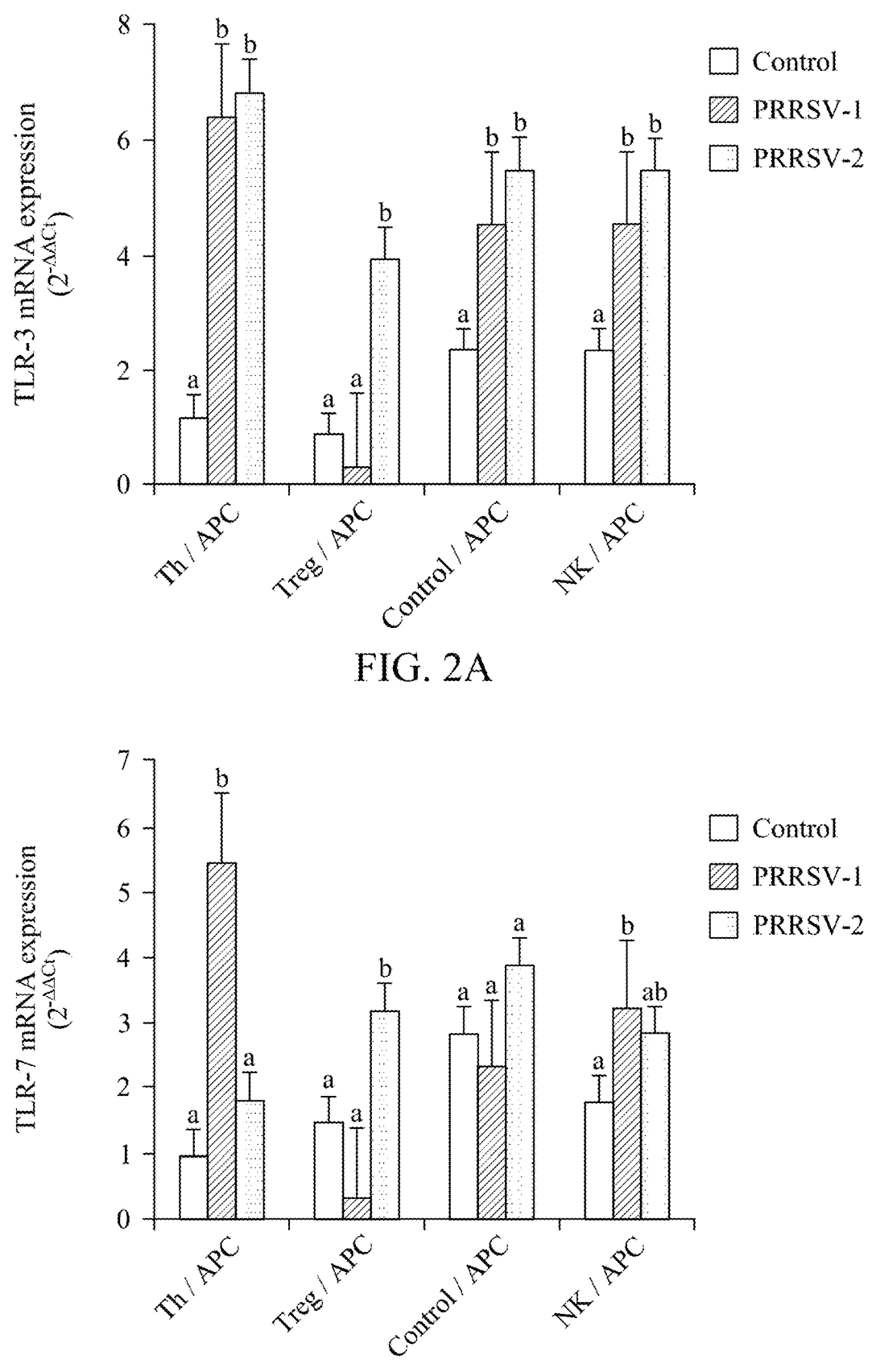
Figure 2C:
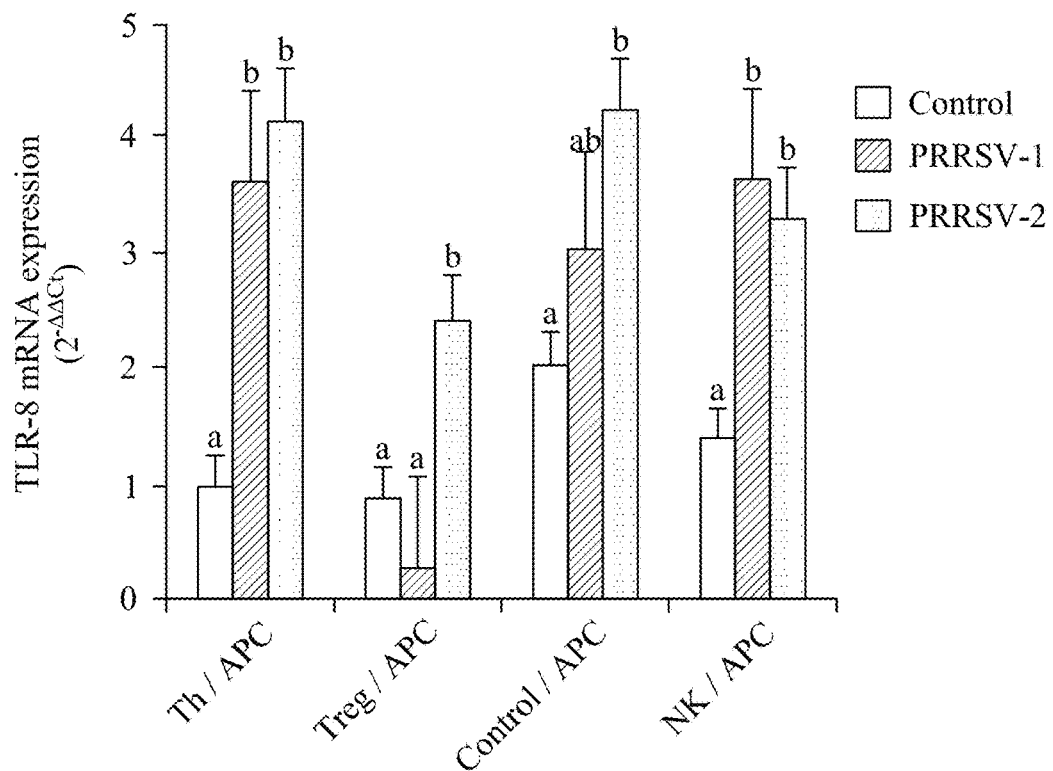

Referring to FIGS. 2A to 2C, which were bar diagrams of mRNA relative expression levels of toll-like receptors (TLRs) 3 (FIG. 2A), TLR 7 (FIG. 2B), and TLR 8 (FIG. 2C) upon the in vitro co-culturation of an antigen-presenting cell with a regulatory T cell, a killer cell, a helper T cell and a control cell, respectively, for an individual pig immunized by various PRRS antigens according to an embodiment of the present invention. mRNA relative expression levels of TLR 3, TLR 7, and TLR 8 in FIGS. 2A to 2C were represented by $-\Delta\Delta Ct$ in the geometric mean ($2^{-\Delta\Delta Ct}$). The statistical significance between two groups ($P<0.05$) was represented by their bars labeled by different letters of FIGS. 2A to 2C.

As shown by the results in FIGS. 2A to 2C, for the pigs immunized with PRRSV-1 and PRRSV-2, the immunological synapse functional expressions of antigen-presenting cells and different T-cell subtypes have been indeed effectively improved, TLR 3, TLR 7, and TLR 8 gene expressions related to virus presenting capability have been improved as well, and the differences between these values had statistical significances.

2.2 Evaluation of Change of Cell Cytokine Level

In this Example, a commercial kit of porcine IL-2 and IL-10 was used for quantifying the IL-2 and IL-10 levels in the porcine cell supernatant. According to the steps of the specification provided in the kit, the standard liquid provided by the kit was diluted for later use, and a flow was described briefly below. Firstly, 100 µL of sample or diluted standard liquid was added into a 96-well plate and incubated for 1 hour. Next, 200 µL of biotinylated antibody reagent was added into the 96-well plate and incubated for another hour. Then, 100 µL of streptavidin-HRP labeled by horseradish peroxidase (HRP) was added therein and incubated for 30 minutes, followed by adding 100 µL of 3,3',5,5'-tetramethylbenzidine (TMB) substrate solution for dark incubation of 30 minutes. Afterwards, 100 µL of stop solution was added to terminate the reaction in order to measure the absorbance. Each well was washed 3 to 5 times with the wash buffer after each incubation step. All steps were performed under the room temperature.

Generally, the absorbance could be read by a commercial continuous spectrophotometer at a wavelength of 450/540 nm, and a standard curve was established by serially-diluted standard solution of various concentrations versus respective absorbances. Then, the cell cytokine concentration of each sample was calculated according to the regression equation of the standard curve, and a commercially statistical software (such as a SAS statistical program) was used to calculate significant difference between the means of all groups, as shown by the results of FIGS. 3A to 3B.

Figure 3A:
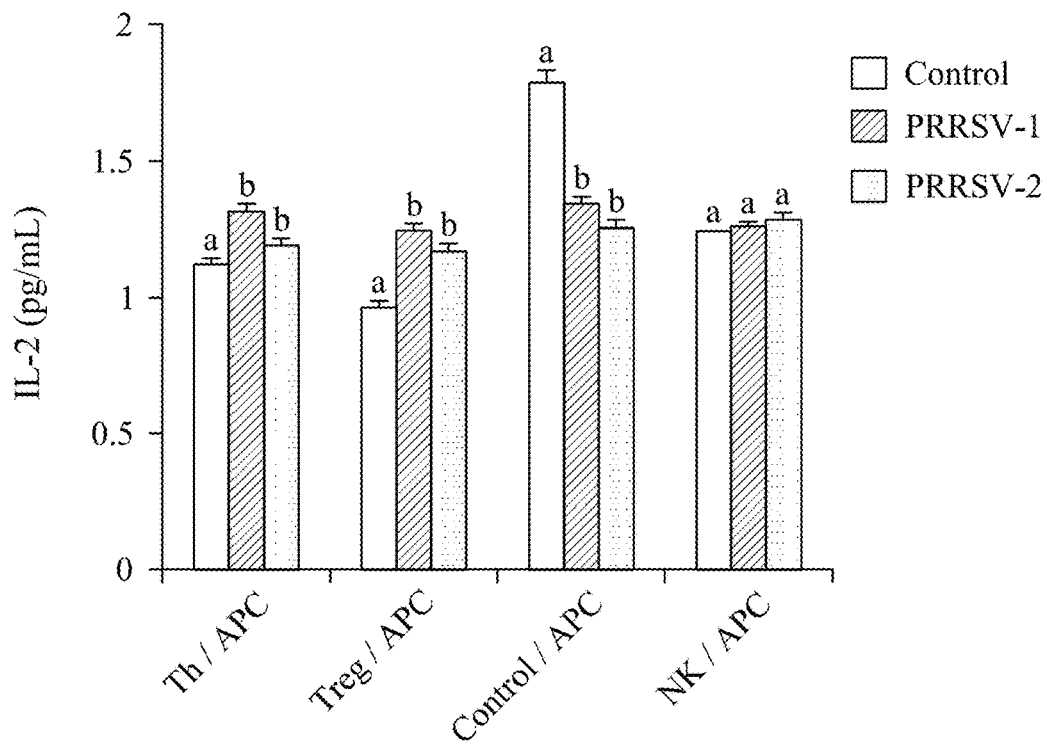
Figures 3B, 4:
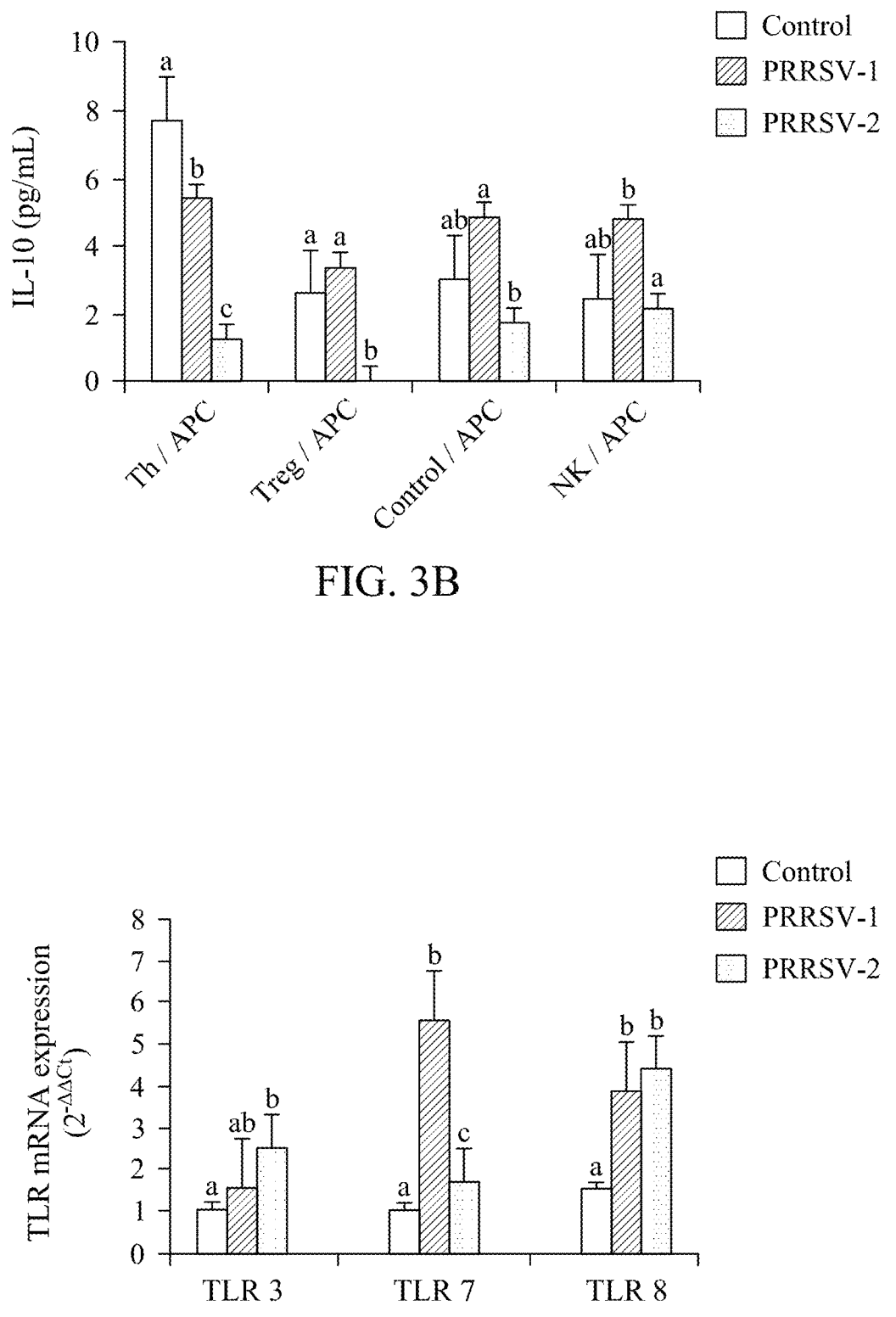

Referring to FIGS. 3A to 3B, which depicted bar diagrams of the IL-2 (FIG. 3A) level and IL-10 (FIG. 3B) level upon the co-culturation of an antigen-presenting cell with a regulatory T cell, a killer cell, a helper T cell and a control cell, respectively, for an individual pig that was immunized by PRRS antigens according to an embodiment of the present invention. The statistical significance between two groups ($P<0.05$) was represented by their bars labeled by different letters of FIGS. 3A to 3B.

As shown by the results of FIGS. 3A to 3B, after the pigs were immunized with PRRSV-1 and PRRSV-2, the IL-2 (having immunoenhancement) level could be effectively increased while the IL-10 (having immunosuppression) level was reduced. Especially when those pigs were immunized by PRRSV-2 containing the T-cell antigen epitope, the IL-10 level was inhibited more significantly, and the differences between these values had statistical significances.

Example 3. Application of In Vitro Immune Synapse System 3.1 Evaluation of Immunogenicity of Antigen Firstly, using the same method as Example 1, alveolar macrophages and sorted T-cell subtypes were isolated from six 4-week-old specific pathogen free (SPF) pigs and co-cultured in a 24-well plate in order to establish an in vitro immune synapse system.

Next, the aforementioned in vitro immune synapse system was added with the antigen protein (the treatment group, 2 µg of PRRSV-1 or PRRSV-2) or without the antigen protein (the control group), and then the system was co-cultured in a $CO_2$ incubator under 37° C. for 24 hours. After the culturation, the 24-well plate was centrifuged at 300×g for 15 minutes, and supernatants were respectively collected for detecting cell cytokines. Meanwhile, a Trizol® reagent (ThermoFisher Scientific) was used to dissolve the cell pellet, and the TLR gene expression was detected in the same method as Example 2, as shown by the result of FIG. 4.

Referring to FIG. 4, which showed a bar diagram of a TLR mRNA relative expression level when the immune adjuvant was screened by an in vitro immune synapse system (including porcine helper T cells and alveolar macrophages) according to an embodiment of the present invention. The statistical significance between two groups ($P<0.05$) was represented by their bars labeled by different letters of FIG. 4.

As shown by the result in FIG. 4, the PRRS antigen (i.e., PRRSV-1 or PRRSV-2) did significantly improve the gene expression levels of TLR 3, TLR 7, and TLR 8 of the immunological synapse, and the differences between these values had statistical significances.

3.2 Evaluation of Immunostimulation of Immune Adjuvant

In addition, after the in vitro immune synapse system (NK/APC or Treg/APC) of Example 1 was co-cultured with an immune adjuvant or not (control group), the IL-2 level was detected by the same method as Example 2. The aforementioned immune adjuvant was poly IC (Sigma-Aldrich) and IL-18 (Sigma-Aldrich Co.). 2 µL of Poly IC (1 mg/mL) (Sigma-Aldrich Co.) was added into the cell sap per well (2 µg/well), or 100 µL IL-18 (1 ng/mL) (Sigma-Aldrich) was added into the cell sap per well (0.1 ng/well). The detection methods for poly IC and IL-18 are referenced from *J. Immunol.* 162 (10):6114-6121 (May 15, 1999) and *J. Immunol.* 176:1348-1354 (2006), which are both incorporated by reference into the present invention.

Figure 5:
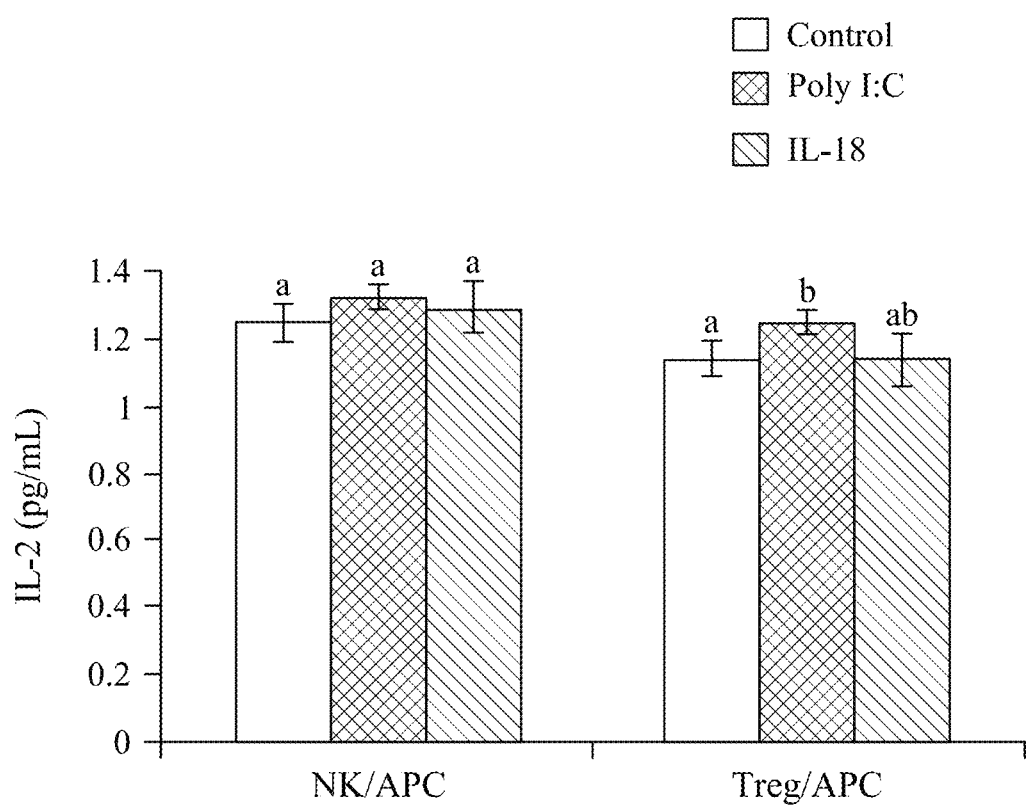
FIG. 5 depicts a bar diagram of the IL-2 level of the immune adjuvant that is screened by an in vitro immune synapse system according to an embodiment of the present invention.

Referring to FIG. 5, which depicted a bar diagram of the IL-2 level (pg/mL) of the immune adjuvant that was screened by an in vitro immune synapse system according to an embodiment of the present invention. The statistical significance between two groups (P<0.05) was represented by their bars labeled by different letters of FIG. 5.

As shown by the result in FIG. 5, the in vitro immune synapse system in which Treg cells matched to APC cells could form the immunological synapse. In comparison to IL-18, the poly-IC could significantly improve the IL-2 level in the immunological synapse, and the differences between these values had statistical significances.

In general, although the present invention utilizes cells from a specific source for establishing the in vitro immune synapse system, specific analysis methods or specific evaluations as examples to illustrate the in vitro immune synapse system of the present invention and the method of in vitro evaluating immune response using the same, any one of ordinary skills in the art of the present invention can realize that the present invention is not limited thereto. Without departing from the spirit and scope of the present invention, cells from other sources can also be used for establishing the in vitro immune synapse system of the present invention and other analyzing methods or other evaluations can also be carried out in the method of in vitro evaluating immune response using the same.

It can be seen from the aforementioned embodiments that an in vitro immune synapse system of the present invention and the method of in vitro evaluating immune response using the same are advantageous in the in vitro immune synapse system containing antigen-presenting cells derived from a same individual pig and several specific T-cell subtypes isolated from peripheral blood mononuclear cells, so as to evaluate the T-cell antigen epitope of a test sample. Through the verification of animal experimentation, the aforementioned in vitro immune synapse system indeed has results consistent with those of animal experimentation. Therefore, when developing new antigens or new adjuvants in the future, the aforementioned in vitro immune synapse system is expected to replace animal experimentation.

Although the present invention has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims.

What is claimed is:

1. A method of in vitro evaluating immune response, comprising:
    providing an in vitro immune synapse system, wherein the in vitro immune synapse system comprises:
    an antigen-presenting cell, wherein the antigen-presenting cell is an alveolar macrophage;
    at least one of a regulatory T cell, a killer cell and a helper T cell, wherein the regulatory T cell has at least a CD4+/CD25+ cell marker, the killer cell has at least a CD4−/CD25+ cell marker, the helper T cell has at least a CD4+/CD25− cell marker; and
    a control cell, wherein the control cell has at least a CD4−/CD25− cell marker, and
    wherein the antigen-presenting cell, the regulatory T cell, the killer cell, the helper T cell and the control cell are primary cell derived from a same individual, and a number of the antigen-presenting cell is 2 to 10 times of a total number of the regulatory T cell, the killer cell and the helper T cell;
    co-culturing a test sample in the immune synapse system for 24 hours; and
    detecting the immune synapse system for an immunization-related change, wherein the immunization-related change comprises a level of toll-like receptor (TLR) gene expression, and
    wherein when any one of the regulatory T cell, the killer cell, the helper T cell has its immunization-related change significantly differ from the immunization-related change of the control cell, the test sample is determined to be immunogenic or immunostimulatory in a porcine respiratory mucosa immune system.

2. The method of in vitro evaluating immune response of claim 1, wherein the test sample comprises an antigen or an adjuvant.

3. The method of in vitro evaluating immune response of claim 1, wherein the same individual is a SPF pig.

4. The method of in vitro evaluating immune response of claim 1, wherein the TLR gene expression level comprises a TLR3 gene expression level, a TLR7 gene expression level, and/or a TLR8 gene expression level.

5. The method of in vitro evaluating immune response of claim 1, wherein the immunization-related change further comprises a cytokine concentration.

6. The method of in vitro evaluating immune response of claim 5, wherein the cytokine concentration comprises an interleukin (IL) concentration.

* * * * *